United States Patent [19]

Nyman et al.

[11] Patent Number: 5,423,880
[45] Date of Patent: Jun. 13, 1995

[54] IMPLANTABLE MEDICAL ELECTRODE DEVICE INCLUDING STRUCTURE FOR EXPLANTING SAME

[75] Inventors: Per Nyman, Djursholm; Anders Lindgren, Taeby, both of Sweden

[73] Assignee: Siemens Elema AB, Solna, Sweden

[21] Appl. No.: 120,808

[22] Filed: Sep. 15, 1993

[30] Foreign Application Priority Data

Sep. 23, 1992 [SE] Sweden ............... 9202746

[51] Int. Cl.⁶ ............................................. A61N 1/05
[52] U.S. Cl. .................................................. 607/122
[58] Field of Search ............... 128/642; 607/119, 120, 607/122, 123, 125–128

[56] References Cited

U.S. PATENT DOCUMENTS

| | | |
|---|---|---|
| 4,574,800 | 3/1986 | Peers-Trevarton . |
| 4,924,881 | 5/1990 | Brewer ........................ 607/127 |
| 5,003,992 | 4/1991 | Holleman et al. ........... 128/642 X |
| 5,179,962 | 1/1993 | Dutcher et al. ............. 128/642 X |

FOREIGN PATENT DOCUMENTS

| | | |
|---|---|---|
| 0368568 | 11/1991 | European Pat. Off. . |
| 2453840 | 5/1976 | Germany ........................ 607/126 |
| WO91/19532 | 12/1991 | WIPO . |

OTHER PUBLICATIONS

"Removal of Chronic Implanted Leads Using a New Technology in 25 Cases", Reinhardt, Eur. J. Card. Pacing & Electrophys., vol. 2, No. 2, Jun. 1992, p. A77.

*Primary Examiner*—Lee S. Cohen
*Assistant Examiner*—Jeffrey R. Jastrzab
*Attorney, Agent, or Firm*—Hill, Steadman & Simpson

[57] ABSTRACT

A medical electrode device, implantable in a subject for electrically stimulating tissue, includes an electrode cable containing an elongated, flexible conductor having an interior channel and covered with electrical insulation, and terminating in an electrode head for engaging tissue of the subject. A stylet is insertable in the channel. The electrode device incorporates structure for assisting in explanting the device formed by an adhesive substance releasably storable within the cable and releasable by manipulation of the stylet or a stylet-like element. When the adhesive is released, the stylet is adhered to the electrode head and can be manipulated from the proximal end of the electrode device to twist the distal end of the electrode device away from in-grown tissue upon explantation.

11 Claims, 2 Drawing Sheets

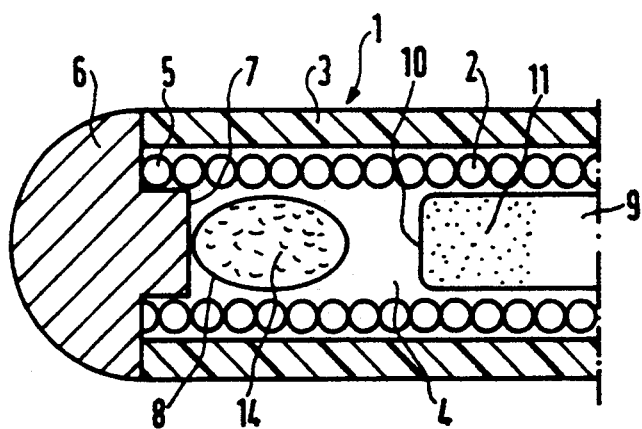
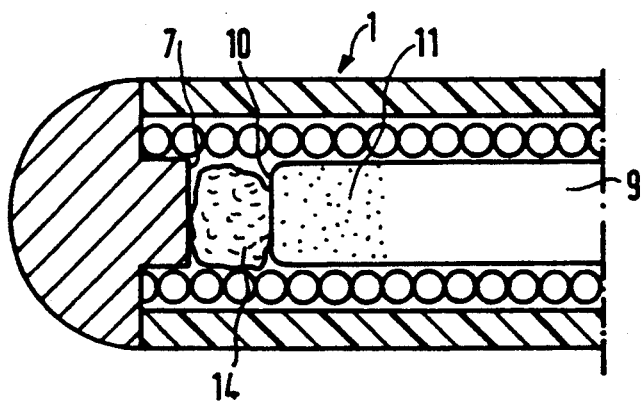

IMPLANTABLE MEDICAL ELECTRODE DEVICE INCLUDING STRUCTURE FOR EXPLANTING SAME

BACKGROUND OF THE INVENTION

1. Field of the Invention

The present invention is directed to a medical electrode device implantable in a subject for stimulating tissue, and in particular to such a device which incorporates means for explanting the device.

2. Description of the Prior Art

Medical electrode devices are well-known in the art for the intracorporeal stimulation of tissue. Such electrode devices include an electrode cable containing an elongated, flexible conductor with an exterior covered by an insulation layer, and an interior forming a channel. The distal end (i.e., the end of the electrode device disposed at the stimulation site) is provided with an electrode head, electrically connected to the conductor. A stylet is insertable into the channel from the distal end (i.e., the end to be connected to a pulse generator) of the electrode device, the stylet normally being used to assist in the implantation of the electrode device, but also being usable, if necessary, to assist in the explantation of the electrode device, should such explantation become necessary.

Such an electrode device which is permanently implanted in a patient, such as a pacemaker electrode, becomes coated over time with connective tissue which anchors the electrode cable in such a way that pulling only on the exposed proximal end of the electrode cable, in order to explant the cable, can be very difficult and even hazardous, because healthy tissue in the area at and around the anchoring site may be torn or otherwise damaged. The physician therefore often elects to leave the electrode cable in place, and to replace it with another cable. Under certain instances, however, removal of the electrode cable is warranted, either by surgery or with aid of an explantation device. Such instances include, for example, the presence of multiple abandoned, disconnected electrode cables in the heart, which can result in the development of infection, or the electrode cables may threaten to puncture a vein or the heart wall.

An explantation device for such an electrode cable is described in the article entitled "Removal of Chronic Implanted Leads Using a New Technology in 25 Cases" Höcherl et al., European Journal of Cardiac Pacing and Electrophysiology, Volume 2, No. 2, June 1992, page A77. In this explantation device, the distal end of a stylet-like member has rearwardly facing projections which substantially flatten against the stylet-like member when the member is introduced into the channel of the electrode cable. The projections subsequently snap outwardly and press against the inner wall of the channel. During explantation, the physician pulls on the member, and the projections then grip the flights of the helically-wound conductor which form the inner wall of the channel. A disadvantage of this known explantation device is that only the small, free end surfaces of the projections engage the interior wall of the channel, and may deform and stretch the helical shape of the conductor to such an extent that the projections lose their grip, at least in part. Another disadvantage of this known device is that the explantation device cannot be repositioned or withdrawn from the channel, because of the projections.

SUMMARY OF THE INVENTION

It is an object of the present invention to provide a medical stimulation device, in the form of an electrode cable of the type described above, which contains an explantation device which is simply and safely attachable within the channel of the electrode cable, while retaining the capability of being re-positionable or completely removable, if desired, from the channel at any time when subjected to a given tractive force.

The above object is achieved in accordance with the principles of the present invention in an electrode cable of the type described above having means for explanting the cable including means contained in the cable for storing an adhesive substance, and means which are manually operable at a proximal end of the cable for selectively releasing the adhesive substance from the means for storing in order to adhere the stylet to the electrode head. The stylet, or a stylet-like member, can then be subjected to loading of varying magnitude before it separates from the electrode cable. This is an advantage, because the physician usually has advance knowledge of the state of the patient's heart. The use of an adhesive material enables the stylet or stylet-like member to be coupled to the proximal side of the electrode head within the electrode channel, thereby completely eliminating the risk of any deformation of the electrode cable when a tractive force is imposed. With the stylet or stylet-like member adhered to the proximal side of the electrode head, the electrode head and the electrode cable can be rotated or twisted around the longitudinal axis of the cable, in order to detach the electrode device from heart tissue. The need to impose critical, tractive forces on the heart tissue is reduced. Even if the styler or stylet-like member is not coupled to the electrode head itself, the adhesive material can couple the stylet or stylet-like member to a number of turns of the helix formed by the conductor within the electrode cable, thereby preventing deformation of the lead in the attachment area during the application of the tractive forces. The adhesive material is preferably a fast-curing, hypoallergenic glue, such as silicone or cyanoacrylate. Other examples of suitable adhesive materials are friction-increasing fluids, congealing wax, coagulating substances or other similar phase-altering chemical components.

In one embodiment of the invention, the adhesive material is enclosed in a rupturable capsule. The capsule is introduced into the channel of the electrode cable, and can be punctured or cracked open using the stylet or the stylet-like member. The capsule can be varied in size in order to contain varying amounts of adhesive material. The capsule may alternatively be disposed at the distal side of the stylet or stylet-like member.

In a further embodiment of the invention, the stylet-like member is tubular, and fits within the channel formed by the conductor. The stylet-like member itself, due to its tubular construction, has an interior channel, and at least the distal end of this channel is filled with the adhesive material. This provides the capability of storing a relatively large amount of adhesive material.

In a preferred embodiment of the invention, the proximal end of the stylet-like member is provided with a device capable of pressing the adhesive material through the channel of the stylet-like member, in the form of a piston-like element slidable in the channel.

With such a device, the physician can extrude as much adhesive as he or she deems necessary for good adhesion of the stylet-like member to the electrode head and/or to flights of the helical conductor. This embodiment also permits the stylet-like member to be positioned at a desired location along the longitudinal length of the channel of the electrode cable, because the adhesive material can be forced out of the channel of the stylet-like member regardless of the position of the member. The stylet-like member can be positioned at a first location, adhesive extruded and permitted to cure, and then can be broken loose from the adhesive with the application of a given tractive force. The stylet-like member can then be repositioned and further adhesive material extruded from the channel of the stylet-like member with the member at the new position.

In a further version of the invention, the stylet or stylet-like member is provided, at least at its distal end, with a surface which, compared to its remaining surface, enhances the adhesiveness of the adhesive material. Such a surface, for example, may have a porous or grooved structure.

DESCRIPTION OF THE DRAWINGS

FIGS 1 and 2 are side sectional views of a first embodiment of an electrode device including means for explanting the electrode device constructed in accordance with the principles of the present invention, respectively showing the adhesive in stored and released states.

DESCRIPTION OF THE PREFERRED EMBODIMENTS

Figure 3:
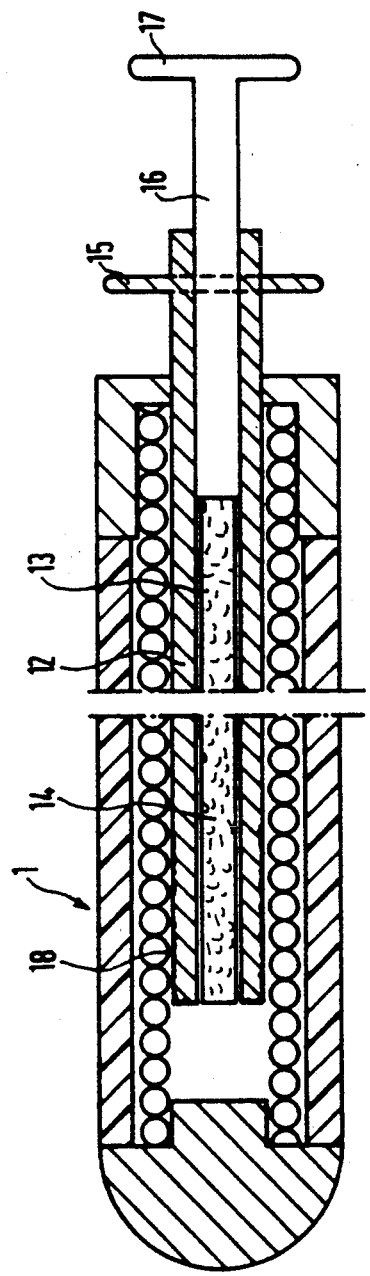
FIGS. 3 and 4 are side sectional views of a further embodiment of an electrode device including means for explanting the electrode device constructed in accordance with the principles of the present invention, respectively showing the adhesive in stored and released states.

The distal end of an electrode device for intracorporeal stimulation of a heart is illustrated in FIG. 1. The electrode device includes an electrode cable 1 containing an elongated, flexible, helical lead 2 having an exterior covered by a layer of insulation 3, and an interior forming a channel 4. The distal end 5 of the lead 2 is connected to an electrode head 6 for stimulating heart tissue in a patient. A rupturable capsule 8, containing an adhesive material 14 such as cyanoacrylate, is disposed within the channel 4 at the proximal side 7 of the electrode head 6. A stylet-like member 9 is also contained in the channel 4. The capsule 8 is preferably attached to the distal end 10 of the member 9. The member 9 and the capsule 8, in combination, form an explantation device. For explantation of the electrode cable 1, the member 9 is inserted further into the channel 4, so that it presses on the capsule 8 until the capsule 8 ruptures, thereby releasing the adhesive material 14 and, when cured, attaching the stylet-like member 9 to the proximal side 7 of the electrode head 6, as shown in FIG. 2. Because the physician, with the aid of the member 9 adhered to the distal end of the cable 1, is able to manipulate the electrode cable 1 at its distal tip, thereby subjecting this portion of the cable 1 to tractive loading, the risk of deforming the conductor 2 is very slight. In this position, it is also possible to rotate the member 9 around its longitudinal axis, thereby also rotating or twisting the electrode cable 1 and the electrode head 6, to assist in detaching the electrode head 6 from heart tissue. In this manner, extraction loads on the heart can be reduced, such loads otherwise possibly causing undesirable deformation of the myocardium during explantation.

At its distal end, the stylet-like member 9 is provided with a surface 11 which, compared to its remaining surface, enhances the adhesiveness of the adhesive material 14. The surface 11 may have a porous or grooved structure. Depending on the composition of the adhesive material 14, the member 9 may be subsequently detachable from the electrode cable 1, given the application of a predetermined tractive load, before heart tissue is damaged.

Figure 4:
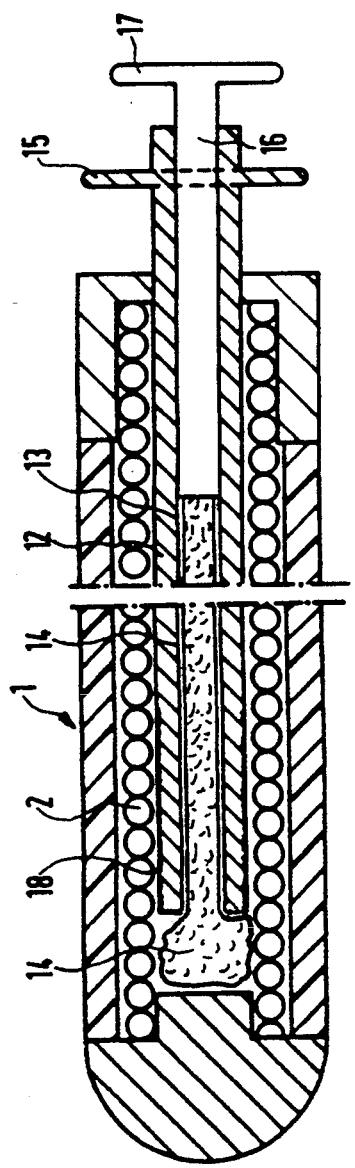

In the embodiment of FIGS. 3 and 4, the distal and proximal parts of the electrode device of FIGS. 1 and 2 are shown, with a different embodiment of the explantation means. The explantation means shown in FIGS. 3 and 4 differs from that shown in FIGS. 1 and 2 by virtue of storage of the adhesive material 14 taking place inside the channel 4 of the electrode cable 1. This occurs by means of the explantation device being formed of a tubular stylet-like member 12. The stylet-like member 12 has a channel 13, formed by the tubular shape of the member 12, which is partially filled with the adhesive material 14. A grip 15 is disposed at a proximal end of the member 12. A slidable plunger 16, having a plate 17 is disposed in the channel 13 of the member 12. The exterior of the plunger 16 slides against the wall of the channel 13.

For explantation of the electrode cable I in the embodiments of FIGS. 3 and 4, the physician presses or extrudes the adhesive material 14 out of the channel 13 of the member 12, as shown in FIG. 4, by pushing the plunger 16 farther into the channel 13 using the grip 15 and the plate 17. The adhesive material, when cured, establishes a firm connection between the member 12 and, for example, the electrode head 6. The electrode cable 1 can then be detached from heart tissue when pulled or twisted in the manner described above. As in the embodiment of FIGS. 1 and 2, the stylet-like member 12 is provided with a surface 18 which enhances the adhesiveness of the adhesive material.

The explantation device shown in FIGS. 3 and 4 can be placed at any desired position along the longitudinal length of the channel 4 of the electrode cable 1. Positioning is accomplished when the adhesive material 14 is extruded out of the channel 13 in the manner described above at an appropriate location along the channel 4, thereby coupling the member 12 to the conductor 2. The adhesive material 14 can couple the member 12 to a number of turns of the helix formed by the conductor 2, thereby preventing deformation of the conductor 2 in the attachment area of the member 13 when the conductor 2 is subjected to tractive loading. The explantation device of FIGS. 3 and 4 can also be repositioned, by applying an elevated tractive force to the attachment site, thereby detaching the member 12 from the adhesive. The member 12 can then be repositioned to a different attachment site, and more adhesive material can then be extruded from the channel 13 of the member 12 and permitted to cure, thereby attaching the member 12 at the new site.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for electrically stimulating tissue implantable in a subject comprising:

an electrode cable containing an elongated, flexible conductor having an interior channel and covered with electrical insulation;

an electrode head connected to said conductor and disposed at a distal end of said cable for engaging tissue of said subject, said electrode head terminating said interior channel and said interior channel being non-communicating with an exterior of said cable at said distal end of said cable;

an explantation element removably inserted in said channel; and means contained in said cable for storing an adhesive substance and means operable from a proximal end of said cable for selectively releasing said adhesive substance from said means for storing into said interior channel for adhering said explantation element said electrode head inside said electrode cable for facilitating explantation of said cable.

2. A device as claimed in claim 1 wherein said adhesive substance is selected from the group consisting of fast-curing, hypoallergenic glues, friction-increasing fluids, congealing waxes, and coagulating substances.

3. A device as claimed in claim 1 wherein said means for storing said adhesive substance comprises a rupturable capsule.

4. A device as claimed in claim 3 wherein said means operable from said proximal end of said cable for selectively releasing said adhesive substance comprises a proximal end of said explantation element.

5. A device as claimed in claim 1 wherein said explantation element comprises a tube, and wherein said means for storing said adhesive substance comprises at least a distal portion of the tube of said explantation element.

6. A device as claimed in claim 5 wherein said means operable from said proximal end of said cable for selectively releasing said adhesive substance comprises a plunger slidable in said tube of said explantation element.

7. A device as claimed in claim 1 wherein said adhesive substance exhibits an adhesiveness, wherein said explantation element has a distal end, and wherein at least said distal end of said explantation element has a surface for enhancing the adhesiveness of said adhesive substance compared to a remainder of the surface of said explantation element.

8. A device for electrically stimulating tissue implantable in a subject comprising:

an electrode cable containing an elongated, flexible conductor having an interior channel and covered with electrical insulation;

an electrode head connected to said electrical conductor disposed at a distal end of said cable for engaging tissue of said subject; said electrode head terminating said interior channel and said interior channel being non-communicating with an exterior of said cable at said distal end of said cable;

a stylet removably inserted in said channel, said stylet having a distal end disposed at said distal end of said cable; and a rupturable capsule containing an adhesive substance disposed in said cable between said electrode head and said distal end of said stylet, said capsule being rupturable by manipulation of said stylet from a proximal end thereof for selectively releasing said adhesive substance into said interior channel for adhering said stylet to said electrode head inside said electrode cable to assist in explanting said electrode cable.

9. A device as claimed in claim 8 wherein said adhesive substance is selected from the group consisting of fast-curing, hypoallergenic glues, friction-increasing fluids, congealing waxes, and coagulating substance.

10. A device for electrically stimulating tissue implantable in a subject comprising:

an electrode cable containing an elongated, flexible conductor having an interior channel and covered with electrical insulation;

an electrode head connected to said conductor and disposed at a distal end of said cable for engaging said tissue of said subject;

a tubular element removably inserted in said channel, said tubular element having a tube therein;

an adhesive substance contained at least in a distal portion of said tube of said tubular element;

a plunger slidable in said tube of said tubular element and manipulable at a proximal end of said cable for selectively discharging said adhesive substance from said tube into said interior channel for adhering said tubular element to said electrode head inside said electrode cable for assisting in explanting said electrode cable.

11. A device as claimed in claim 10 wherein said adhesive substance selected from the group consisting of fast-curing, hypoallergenic glues, friction-increasing fluids, congealing waxes, and coagulating substances.

* * * * *